(12) United States Patent
Meier et al.

(10) Patent No.: US 7,516,664 B2
(45) Date of Patent: Apr. 14, 2009

(54) METHOD FOR THE ULTRASOUND TESTING OF A WORKPIECE WITHIN A CURVED REGION OF ITS SURFACE AND DEVICE SUITABLE FOR THE EXECUTION OF THE PROCESS

(75) Inventors: Rainer Meier, Erlangen (DE); Jana Becker, Möhrendorf (DE); Thomas Rehfeldt, Möhrendorf (DE)

(73) Assignee: Intelligendt Systems & Services GmbH & Co. KG, Erlangen (DE)

( * ) Notice: Subject to any disclaimer, the term of this patent is extended or adjusted under 35 U.S.C. 154(b) by 49 days.

(21) Appl. No.: 11/710,889

(22) Filed: Feb. 26, 2007

(65) Prior Publication Data
US 2007/0227249 A1 Oct. 4, 2007

(30) Foreign Application Priority Data
Mar. 4, 2006 (DE) .................. 10 2006 010 010

(51) Int. Cl.
*G01N 29/04* (2006.01)
(52) U.S. Cl. .............. 73/644; 73/615; 73/616; 73/637
(58) Field of Classification Search .......... 73/622–628, 73/614–616, 632–633, 637–640, 643–644
See application file for complete search history.

(56) References Cited

U.S. PATENT DOCUMENTS

| | | | |
|---|---|---|---|
| 4,472,973 A | | 9/1984 | Sugai et al. |
| 4,472,975 A | | 9/1984 | Beck et al. |
| 4,532,796 A | * | 8/1985 | Martens et al. ........... 73/632 |
| 4,848,159 A | | 7/1989 | Kennedy et al. |
| 5,024,093 A | * | 6/1991 | Sasaki et al. ............. 73/633 |
| 5,060,652 A | * | 10/1991 | Umemura et al. ......... 600/447 |
| 5,583,292 A | * | 12/1996 | Karbach et al. ........... 73/638 |
| 5,585,565 A | * | 12/1996 | Glascock et al. .......... 73/644 |
| 6,161,435 A | * | 12/2000 | Bond et al. ............... 73/587 |
| 6,443,011 B1 | * | 9/2002 | Schulze et al. ........... 73/622 |
| 6,957,583 B2 | * | 10/2005 | Tooma et al. ............. 73/625 |

(Continued)

FOREIGN PATENT DOCUMENTS

DE 196 17 455 A1 11/1997

(Continued)

*Primary Examiner*—Helen C. Kwok
(74) *Attorney, Agent, or Firm*—Laurence A. Greenberg; Werner H. Stemer; Ralph E. Locher

(57) ABSTRACT

In a method for the ultrasonic testing of a workpiece (2) in a curved area of its surface, in particular of a workpiece (2) made of a fiber composite material, an ultrasonic test head (10) is acoustically coupled to the workpiece in this area, and includes an ultrasonic transducer arrangement (12) comprising a plurality (N) of individually driveable transducer elements ($20_i$) which are arranged next to one another. In chronologically successive test cycles, a number (n) of transducer elements ($20_i$) are respectively combined to form a group and are driven in a plurality of test pulses within this test cycle in a time delayed manner with respect to one another such that the transmitted ultrasound beam (30a-d) in this test cycle is swept within a predetermined angular range ($\alpha 1$, $\alpha 2$), so that one of the number of echo signals, corresponding to the number of test pulses, for each group is received from different directions of the workpiece (2).

18 Claims, 2 Drawing Sheets

U.S. PATENT DOCUMENTS 7,010,980 B2 * 3/2006 Meier .................. 73/602
2004/0016299 A1 1/2004 Glascock et al.

FOREIGN PATENT DOCUMENTS

| | | | |
|---|---|---|---|
| DE | 198 37 262 A1 | 3/2000 | |
| EP | 0 068 389 A1 | 1/1983 | |
| EP | 1 398 627 A2 | 3/2004 | |
| WO | 00/09014 | 2/2000 | |

* cited by examiner

METHOD FOR THE ULTRASOUND TESTING OF A WORKPIECE WITHIN A CURVED REGION OF ITS SURFACE AND DEVICE SUITABLE FOR THE EXECUTION OF THE PROCESS

BACKGROUND OF THE INVENTION

Field of the Invention

The invention relates to a method for the ultrasonic testing of a workpiece in a curved area of its surface, in particular of a workpiece made of a fiber composite material. In addition, the invention relates to a test arrangement suitable for carrying out the method.

Especially workpieces manufactured from fiber composite materials such as glass-fiber-reinforced or carbon-fiber-reinforced plastics (GFP or CFP) can have high porosity or delaminations attributable to the respective manufacturing method chosen. This is a significant problem in particular in mechanically highly-stressed and safety-relevant components.

Gundtoft, Hans Erik, "Quantitative material characterisation of composites by ultrasonic scanning", 15$^{th}$ WCNDT Conference Rome 2000, published on the Internet at www.ndt.net/article/wcndt00/papers/idn531/idn531.htm, discloses a method for determining the porosity of a fiber composite material, in which an ultrasound signal is injected into the component, the amplitude of the backwall echo signal is detected and compared with the corresponding signals of a flaw-free component. Here, a lower amplitude of the backwall echo ultrasound signal is a sign of the presence of porous places inside the component.

Shark L.-K., Yu, C., "Automatic estimation of ultrasonic attenuation for porosity evaluation in composite material", 15$^{th}$ WCNDT Conference Rome 2000, furthermore discloses correction of the backwall echo signal by a so-called wavelet analysis, wherein the ratio between amplitude of the entry echo signal and amplitude of the corrected backwall echo signal is used to assess the porosity.

The known methods presuppose, however, that the components to be tested have a planar surface and a backwall which is essentially parallel thereto in order to receive a backwall echo which can be evaluated. One particular problem, however, is the automated testing of components in non-planar areas in particular which are, on account of their manufacture, particularly susceptible to flaws, for example in curved radii areas or in areas in which the component is stiffened by stringers. In order to obtain reliable test results in these areas, too, it remains necessary to carry out manual tests using individual oscillator test heads.

SUMMARY OF THE INVENTION

The invention is now based on the object of providing a method for the ultrasonic testing of a workpiece in a curved area of its surface, in particular of a workpiece made of a fiber composite material, with the use of which method extensive automation of the test is possible with high testing quality. In addition, the invention is based on the object of providing a test arrangement suitable for carrying out the method.

With respect to the method, the stated object is achieved according to the invention, wherein an ultrasonic test head is acoustically coupled to the workpiece in a curved area of its surface, and includes an ultrasonic transducer arrangement comprising a plurality of individually driveable transducer elements which are arranged one next to the other, wherein, in chronologically successive test cycles, a number of transducer elements are respectively combined to form a group and are driven using a plurality of test pulses within this test cycle in a time delayed manner with respect to one another such that the transmitted ultrasound beam in this test cycle is swept within a predetermined angular range, so that one of the number of echo signals, corresponding to the number of test pulses, for each group is received from different directions of the workpiece. Since echo signals from different directions of the workpiece can be analyzed, the qualitative assessment of the workpiece, such as with respect to its porosity or with respect to the presence of delaminations, is improved.

If the echo signals of the test pulses are used for assessment purposes, in which test pulses a backwall echo signal received from a backwall and/or an entry echo signal received from a surface are/is at a maximum, reliable statements can be made about the porosity or delamination of the workpiece.

In one preferred refinement of the method, an ultrasonic transducer arrangement having a curved transmitting and receiving face which is matched to the curvature of the surface is used.

If the acoustic coupling is effected via a water initial segment, it is possible to inject the ultrasound produced by the ultrasonic transducer arrangement into the workpiece without losses, even on non-planar, uneven surfaces.

In one preferred refinement of the method, the distance from the ultrasonic test head to the surface is varied. It is thereby possible to limit the necessary angular range and accordingly the number of test pulses necessary in each test cycle to a degree required for finding the maximum backwall echo.

With respect to the test arrangement, the stated object is achieved according to the invention by a test arrangement whose advantages correspond to the advantages which are stated for the respectively associated method claims. Advantageous refinements of this test arrangement are additionally described in the present application.

BRIEF DESCRIPTION OF THE DRAWINGS

For the purposes of explaining the invention in more detail, reference is made to the exemplary embodiment of the drawing, in which.

DESCRIPTION OF THE PREFERRED EMBODIMENTS

Figure 1:
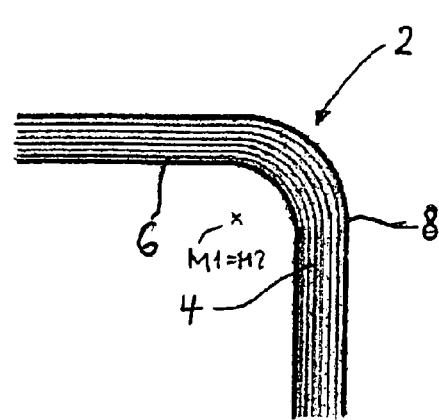
FIGS. 1-3 each show a schematic sectional view of a workpiece made of a fiber composite material in a curved area of its surface.

According to FIG. 1, a workpiece 2 made of a fiber composite material, for example a CFP component, comprises a plurality of fiber layers 4 which are laminated onto each other. The workpiece 2 has a curved surface area, the illustrated example illustrating an ideal situation in which the center of curvature M1 of the radius of the inner concave surface 6 matches the center of curvature M2 of the radius of the outer concave surface 8, such that an ultrasound beam injected in a perpendicular fashion into the outer surface 8 in this area also strikes the inner surface 6 (the backwall) in a perpendicular fashion.

Figure 2:
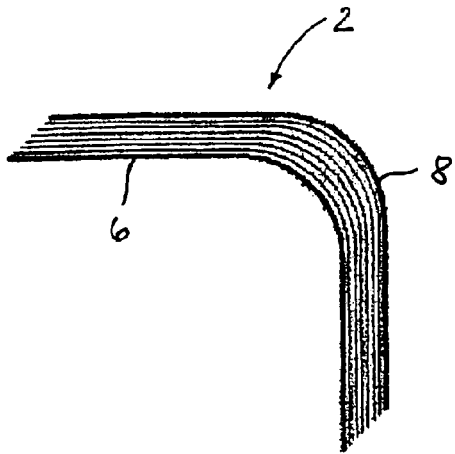

Such an ideal situation is generally not encountered in practice, however. FIG. 2 shows a situation as can be frequently observed, in which the inner surface 6 and the outer surface 8 have radii areas which are no longer concentric to one another, with the result that it is no longer inevitable that an ultrasound beam injected in a perpendicular fashion into the outer surface 8 also strikes the inner surface 6 in a perpendicular fashion.

Figure 3:
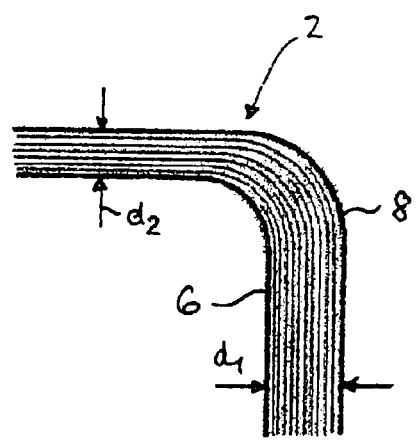

Another situation frequently encountered in practice is illustrated in FIG. 3. Here, the curved area forms a transition zone between two areas of the workpiece 2, which have differing thicknesses $d_1$ and $d_2$.

Figure 4:
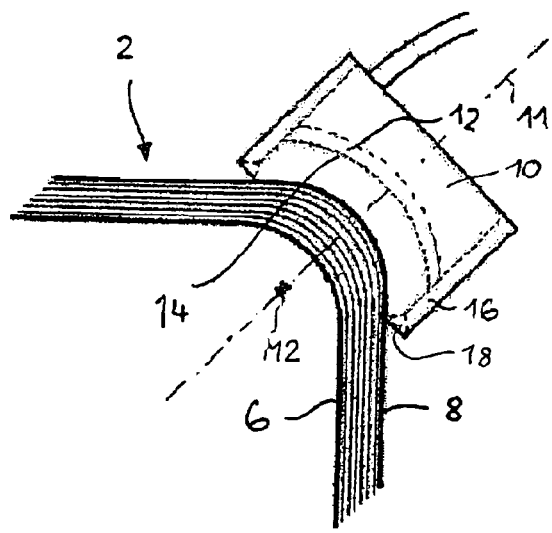
FIG. 4 shows the workpiece according to FIG. 2 having a test arrangement which is schematically represented and fitted in the radii area.

According to FIG. 4, a test arrangement according to the invention is mounted on the curved area of the surface of the workpiece 2 illustrated in FIG. 2. The test arrangement includes an ultrasonic test head 10 which is centered on the workpiece 2 in a manner such that its mid-axis 11 intersects the center M2 of the radius of the outer surface 8. An ultrasonic transducer arrangement 12, whose transmitting and receiving face 14 has a radius of curvature which is matched to the radius of curvature of the outer surface and is concave in the example, is arranged in the ultrasonic test head 10. In the ideal case, this radius of curvature and also the distance from the transmitting and receiving face 14 to the outer surface 8 with correctly positioned ultrasonic test head 10 are selected such that the center of its radius coincides with the center M2 of the radius of curvature of the outer surface 8.

The ultrasonic test head 10 is arranged in a water chamber 16 such that a water-filled initial segment is located between the transmitting and receiving face 14 and the outer surface 8. Sealing lips 18 at the edge of the water chamber 16 ensure that the supplied amount of water into the water chamber 16 necessary to maintain the water anterior segment is as small as possible.

Figure 5:
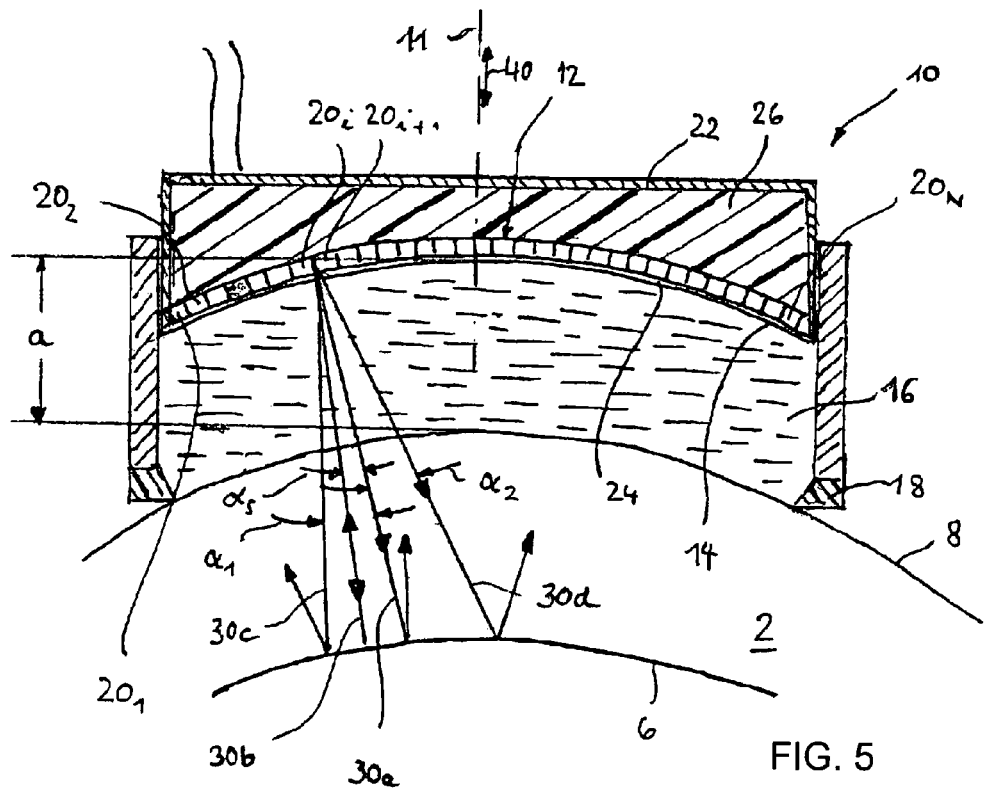
FIG. 5 shows a schematic sectional view of a test arrangement in a position fitted on a workpiece.

According to FIG. 5, the ultrasonic transducer arrangement 12 includes a plurality N, for example N=32, of piezoelectric transducer elements $20_1, 20_2, \ldots 20_N$, which are arranged in a housing 22 next to one another along a concave line (bent linear transducer array). A $\lambda/4$ matching layer 24 is arranged on its transmitting and receiving face, and ensuring acoustic matching between the oscillator material of the transducer elements $20_1$-$20_N$ and the coupling medium which serves as the initial segment (water in the exemplary embodiment). The transducer elements $20_1$-$20_N$ adjoin a damping body 26, which is arranged in the housing 22, on its rear face averted from the transmitting and receiving face.

The transducer elements $20_1$-$20_N$ can be driven independently of each other. A number n of transducer elements $20_1$-$20_N$, preferably two to four neighboring transducer elements $20_1$-$20_N$, can in each case be combined in one test cycle to form a group. The exemplary embodiment illustrates a situation in which two neighboring transducer elements $20_i$ and $20_{i+1}$ are combined to form a group in one such test cycle. In this test cycle, using a plurality of test pulses, the respective individual transducers $20_i$ and $20_{i+1}$ are driven in a time delayed manner with respect to one another with different delay times such that the ultrasound beam emitted by them can be swept within an angular range $\alpha_1, \alpha_2$.

FIG. 5 shows one situation in which, where the time delay (time difference) $\Delta t$ between transducer elements $20_i$ and $20_{i+1}$ equals zero, the ultrasound beam 30a emitted by the two transducer elements $20_i$ and $20_{i+1}$ in a perpendicular fashion to the transmitting and receiving face 14 strikes the outer surface 8 of the workpiece 2 in a perpendicular fashion, but does not strike its inner surface 6 in a perpendicular fashion and is thus reflected by this inner surface 6 at an oblique angle, with the result that the associated backwall echo is not received by the two transducer elements $20_i$ and $20_{i+1}$, or only at low signal strength. Because the individual elements $20_i$ and $20_{i+1}$ are driven in a time delayed manner, the emission angle $\alpha$ varies successively in steps of, for example, 2° in both directions and the respectively associated echo signals are received. The angular range $\alpha_1, \alpha_2$ is approximately 20° (for example symmetrically about $\alpha=0°$ where $\alpha_1=\alpha_2=10°$) such that 11 test pulses occur within the test cycle 11. It can be seen in the figure that a situation arises at least approximately for an emission angle $\alpha_s$ in which the ultrasound beam 30b, which is emitted in the test pulse s and propagates at an angle $\alpha_s$ to the normal to the transmitting and receiving face 14, strikes the inner surface 6 in an approximately perpendicular fashion, with the result that the backwall echo emitted by the inner surface 6 is received by the two transducer elements $20_i$ and $20_{i+1}$ at maximum signal strength. This echo signal with the maximum signal strength of the backwall echo signal is then used for further evaluation by comparing for example the signal amplitude of the backwall echo signal with the signal amplitude of the entry echo signal reflected by the outer surface 8, for example by forming ratios. In this forming of ratios, the entry echo signal of that test pulse in which this is a maximum is preferably used, in the example at a sweep angle $\alpha=0°$. The ultrasound beams 30c and 30d, which are respectively emitted at the sweep angles $\alpha_1$ and $\alpha_2$, are likewise reflected on the inner surface 6 such that they are virtually no longer received by the transducer elements $20_i$ and $20_{i+1}$ of the active group.

FIG. 5 does not show any refraction of the ultrasound beams 30a-d on the outer surface 8, for reasons of clarity.

FIG. 5 shows a situation in which the curvature of the transmitting and receiving face 14 of the ultrasonic transducer arrangement 12 and of the ultrasonic test head 10 has a radius which is larger than the radius of the outer surface 8, is shown idealized as constant and in which, if the time difference which is used to drive the transducer elements $20_i$ and $20_{i+1}$ forming one group equals zero, the ultrasound beam emitted by said transducer elements strikes the outer surface 8 in a perpendicular fashion. This presupposes that the distance a between transmitting and receiving face 14 and outer surface 8 corresponds to the difference between these two radii and that the centers of their radii coincide. In order to permit this within certain limits, the ultrasonic test head 10 is arranged with its ultrasonic transducer arrangement 12 axially in the water chamber 16, i.e. such that it can move in the direction of the mid-axis 11 of the ultrasonic transducer arrangement 12, as is illustrated by the double arrow 40. This measure can be used to compensate for differences in the radii of curvature of the outer surface 8, so that the angular range necessary in the test cycle can be minimized. For example, if the radius of curvature of the outer surface 8 is slightly larger, a concentric situation—ideal positioning of the ultrasonic test head 10 and ideal curvature of the outer surface 8 in the form of a circular arc are presupposed—can be caused by the ultrasonic test head 10 in the water chamber 16 being moved axially toward the outer surface 8, i.e. its distance a from this surface 8 is changed. It is thereby possible to test a component with a radius of curvature which changes in one direction perpendicular to the plane of curvature (plane of the drawings of FIGS. 1-5), for example a spar of a vertical stabilizer of an aircraft, using a single test arrangement by changing the distance a in this longitudinal direction at the same time as the movement of the test arrangement.

In the case of non-ideal radii, the distance from the transmitting and receiving face of the transducer elements forming a respective group to the outer surface 8 is not constant. The changing initial segment in the water chamber 16 causes a time shift in the echo signals. This hampers the evaluation of the measurement signals in the case of an image, for example a B-mode image. In order to determine the time window for the echo signals that is suitable for a group, an individual transducer element $20_i$, whose ultrasound beam is emitted in a large angular range and which is used to determine the distance from this transducer element $20_i$ to the outer surface 8, is driven in a preceding measurement step. Said distance or the associated run time is used to fix the time window for the echo signal of those groups which are adjacent to said transducer element $20_i$, for example the group $20_{i-2}$, $20_{i-1}$ to $20_{i+1}$, $20_{i+2}$.

Figure 6:
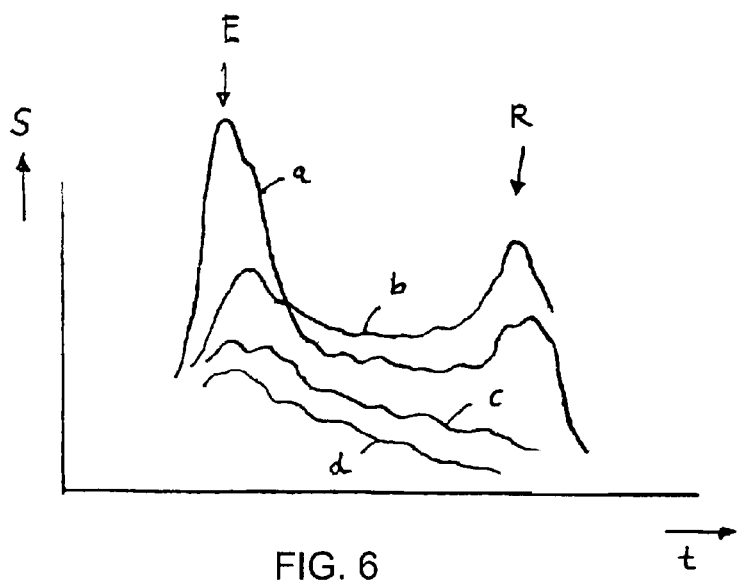
FIG. 6 shows a broadly schematic simplified diagram in which the echo signals S received by the ultrasonic transducer arrangement in different test pulses in a test cycle are plotted against the run time t.

The graph in FIG. 6 illustrates the echo signals S, which are received by a group in different second test pulses in each case as a function of the run time, for four test pulses within one test cycle by way of example. Curve a shows a situation in which the ultrasound beam strikes the outer surface 8 in a perpendicular fashion, but does not strike the inner surface 6 in a perpendicular fashion (time difference $\Delta t=0$, associated ultrasound beam 30$a$). Thus, a high entry echo signal E is produced with relatively low backwall echo signal R. Curve b represents the situation as it is measured using the ultrasound beam 30$b$. The entry echo signal E is significantly reduced, while the backwall echo signal R is at a maximum. Curves c and d show situations in which the ultrasound beams 30$c$ and 30$d$ strike neither the outer surface 8 nor the inner surface 6 at right angles, so that neither entry echo signal E nor backwall echo signal R are at a maximum. The echo signals of curves a and b, i.e. the echo signals of the test pulses belonging to the sweeping angles 0° and $\alpha_s$, are then used for the evaluation by dividing for example the signal amplitude of the backwall echo signal R of the test pulse producing the curve b by the signal amplitude of the entry echo signal E of the test pulse producing the curve a.

We claim:

1. A method for an ultrasonic testing of a workpiece in a curved surface area thereof, the method which comprises:
   providing an ultrasonic test head with an ultrasonic transducer configuration having a plurality of individually driveable transducer elements arranged next to one another;
   acoustically coupling the ultrasonic test head to the workpiece in the curved surface area;
   respectively combining, in chronologically successive test cycles, a number of transducer elements to form a group and driving the transducer elements in a plurality of test pulses within the test cycle in a time-delayed manner with respect to one another, and to sweep a transmitted ultrasound beam in the test cycle within a predetermined angular range, so that each group receives a number of echo signals corresponding to a number of test pulses from different directions of the workpiece; and
   determining which test pulse results in a backwall echo signal maximum, and using the echo signals of the test pulse for assessment purposes for which the backwall echo signal received from a backwall is at a maximum.

2. The method according to claim 1, which comprises testing the workpiece made of a fiber composite material.

3. The method according to claim 1, which comprises providing the ultrasonic transducer configuration with a curved transmitting and receiving face matched to a curvature of the curved surface area.

4. The method according to claim 1, which comprises using a water initial segment to effect the acoustic coupling.

5. The method according to claim 4, which comprises determining which test pulse results in a backwall echo signal maximum, and using the echo signals of the test pulse for assessment purposes for which the backwall echo signal received from a backwall is at a maximum, and varying a distance from the test head to the curved surface area.

6. A test configuration for carrying out the method according to claim 1, comprising: an ultrasonic test head including an ultrasonic transducer configuration formed with a plurality of individually driveable transducer elements disposed next to one another, and wherein said ultrasonic test head can be moved in a direction of a mid-axis thereof in a water chamber serving as an initial segment.

7. The test configuration according to claim 6, wherein the water chamber is open on a coupling face averted from said ultrasonic test head and an edge surrounding the coupling face is provided with an elastic sealing lip.

8. The test configuration according to claim 6, wherein said ultrasonic transducer configuration has a curved transmitting face.

9. The method according to claim 4, which comprises determining which test pulse results in a maximum entry echo signal received from the curved surface area, and using the echo signals of the test pulse for assessment purposes for which the entry echo signal received from the curved surface area is at a maximum, and varying a distance from the test head to the curved surface area.

10. A method for an ultrasonic testing of a workpiece in a curved surface area thereof, the method which comprises:
    providing an ultrasonic test head with an ultrasonic transducer configuration having a plurality of individually driveable transducer elements arranged next to one another;
    acoustically coupling the ultrasonic test head to the workpiece in the curved surface area;
    respectively combining, in chronologically successive test cycles, a number of transducer elements to form a group and driving the transducer elements in a plurality of test pulses within the test cycle in a time-delayed manner with respect to one another, and to sweep a transmitted ultrasound beam in the test cycle within a predetermined angular range, so that each group receives a number of echo signals corresponding to a number of test pulses from different directions of the workpiece;
    determining which test pulse results in a maximum entry echo signal received from the curved surface area, and using the echo signals of the test pulse for assessment purposes for which the entry echo signal received from the curved surface area is at a maximum.

11. The method according to claim 10, which comprises testing the workpiece made of a fiber composite material.

12. The method according to claim 10, which comprises providing the ultrasonic transducer configuration with a curved transmitting and receiving face matched to a curvature of the curved surface area.

13. The method according to claim 10, which comprises using a water initial segment to effect the acoustic coupling.

14. The method according to claim 13, which comprises determining which test pulse results in a backwall echo signal maximum, and using the echo signals of the test pulse for assessment purposes for which the blackwall echo signal received from a backwall is at a maximum, and varying a distance from the test head to the curved surface area.

15. A test configuration for carrying out the method according to claim 10, comprising: an ultrasonic test head including an ultrasonic transducer configuration formed with a plurality of individually driveable transducer elements disposed next to one another, and wherein said ultrasonic test head can be moved in a direction of a mid-axis thereof in a water chamber serving as an initial segment.

16. The test configuration according to claim 15, wherein the water chamber is open on a coupling face averted from said ultrasonic test head and an edge surrounding the coupling face is provided with an elastic sealing lip.

17. The test configuration according to claim 15, wherein said ultrasonic transducer configuration has a curved transmitting face.

18. The method according to claim 13, which comprises varying a distance from the test head to the curved surface area.

* * * * *